United States Patent [19]

Boss

[11] Patent Number: 5,069,417
[45] Date of Patent: Dec. 3, 1991

[54] APPARATUS FOR PRODUCING A CURED-IN-PLACE TEST SAMPLE OF CONCRETE

[76] Inventor: Richard J. Boss, 19015 36th Avenue West, Suite C, Lynnwood, Wash. 98036

[21] Appl. No.: 553,440

[22] Filed: Jul. 13, 1990

[51] Int. Cl.$^5$ .......................... G01N 1/04; B28B 7/12
[52] U.S. Cl. .................................... 249/74; 249/66.1; 249/136; 249/DIG. 4; 425/437; 425/443
[58] Field of Search ............................. 425/437, 443; 249/DIG. 4, 66.1, 74, 76, 136

[56] References Cited

U.S. PATENT DOCUMENTS

| | | | |
|---|---|---|---|
| 3,151,374 | 10/1964 | Kersten | 249/66.1 |
| 3,176,053 | 3/1965 | Di Stasio | 249/DIG. 4 |
| 3,418,767 | 12/1968 | Seeger | 249/66.1 |
| 3,432,027 | 3/1969 | Mueller | 249/74 |
| 3,939,234 | 2/1976 | Dashew | 425/437 |
| 3,958,790 | 5/1976 | Scott | 249/66.1 |
| 4,047,690 | 9/1977 | Winter et al. | 249/137 |
| 4,365,784 | 12/1982 | De Stasio | 249/DIG. 4 |

Primary Examiner—James C. Housel
Attorney, Agent, or Firm—Christensen, O'Connor, Johnson & Kindness

[57] ABSTRACT

An apparatus for providing a test sample of concrete from a large poured area of concrete includes a mold suitable for placement within the concrete form, said mold including a continuous sidewall and a bottom wall connected to the sidewall. An insert within said mold is spaced from the bottom wall so that a pressurization chamber is formed between the insert and the bottom wall of the mold. A fluid inlet is formed in the mold in fluid communication with the pressurization chamber and a fluid inlet tube is connected at a first end thereof to the fluid inlet. Preferably, the fluid tube is of a length sufficient to reach the surface of the concrete poured within the form. In one embodiment, a plurality of legs are formed on the insert to maintain the spacing of the insert from the bottom wall of the mold, the legs being separated sufficiently to allow fluid flow between them. In another embodiment, the space between the insert and the bottom of the mold is filled with a noncompressible fluid. The method of producing a test sample from a pour of concrete includes the steps of defining a test sample at the time of pouring the concrete in the mold, maintaining an open space beneath said test sample while said concrete is being poured, and, after the concrete has cured, pressurizing said space sufficiently to force said test sample from the pour. The test sample, once it is removed from the concrete pour, can then be taken to a laboratory and tested by conventional techniques.

15 Claims, 2 Drawing Sheets

APPARATUS FOR PRODUCING A CURED-IN-PLACE TEST SAMPLE OF CONCRETE

BACKGROUND OF THE INVENTION

This invention relates to concrete testing methods and apparatus and, more particularly, provides a method and apparatus for producing a test sample of concrete that is poured in place and later removed for testing.

In the construction of highways, buildings, and other structures utilizing concrete, it is necessary from time to time to test the strength of a sample of the poured concrete after it has cured to ensure that it has sufficient structural strength required for a particular installation. The most common method of testing concrete has been to produce a concrete test cylinder by pouring fresh concrete into a cylindrical mold, separate from the actual pour, consolidating it, and then leaving it to set. The following day the cylinders are picked up and delivered to a laboratory where the molds are removed and the cylinders are cured under laboratory conditions. After curing, the cylinders are tested for compressive strength at some specified time, most commonly the time at which a particular process is to be accomplished at the building site in which the concrete strength becomes a relevant factor. The use of separately poured and cured test cylinders is a long-used system and demonstrates the potential strength of concrete but is found to have certain drawbacks.

Laboratory test cylinders are largely ineffective in representing the in-place strength of concrete in that they are cured under circumstances that are entirely different from those to which the concrete poured in the field is subjected. The differences between the laboratory test cylinder and the actual concrete in the field have been demonstrated to be significantly more acute early in the setting cycle (less than two weeks) than they are late in the cycle (longer than one month). In today's fast-track construction process, it is critical to maintaining the schedule that early concrete strengths be accurately determined to allow for such activities as form and shoring removal, post-tensioning, panel tilting, and other activities. All of these activities need to be performed as early as the strength of the concrete will allow in order to facilitate the schedule but, if performed too early, pose severe safety hazards and jeopardize both the schedule and cost of the project by making failure of the structure possible when loads are applied or shoring is removed. Therefore, it is essential to be able to obtain accurate and timely information as to the strength of the actual concrete in place.

Concrete gains strength through an exothermic reaction between the cement and the mixing water. As in all such reactions, material temperatures are a major determining factor in the speed with which the reaction and corresponding strength gain occur. Because laboratory-cured test specimens are cured at temperatures often completely different from those of the work in the field, they often cannot represent the actual in-place strength. In an effort to solve some of the problems in laboratory-cured test samples, other systems have been tried to achieve a better representation of the in-place strength of the concrete. Presently, the most widely used alternate method for producing a test cylinder is the field-test cylinder. The field-test cylinder is essentially the same as the lab test cylinder in form but, rather than being cured in the laboratory, is left out in the field with the work until an activity requiring a given strength is scheduled. The field-test cylinder is then taken to the laboratory to be tested. The use of the field-test cylinder often produces test results that are more representative of the early in-place strengths of the concrete than are the lab-cured cylinders but there are still some serious drawbacks. The field-test cylinders are a completely different mass from the work in place. Testing professionals argue that this difference in mass allows the weather conditions, particularly if adverse, to have a much greater effect on the field-cured test cylinders than they do on the actual work in place.

Other methods for quick in-place testing of concrete utilize impact rebound hammers or probes shot from powder-actuated devices that actually impact the in-place concrete. Also, at times, rods are placed in the fresh concrete to be tension-removed later as an indicator of strength. The accuracy and simplicity of these methods have always been questioned and they have not gained widespread acceptance. One system for in-place testing that does work well is a system wherein a thermocouple is placed in the actual poured concrete to monitor the curing temperature. The thermocouple output is connected to a microprocessor controller that, in turn, controls a heater in a metal mold. A test sample of concrete is poured into the metal mold and the microprocessor, using the data gathered by the thermocouple in the actual workpiece, controls the temperature of the mold so that the concrete in the metal test mold is at the same temperature as the actual work in place as it cures. Using a heat-controlled test mold produces a sample that provides accurate data as to concrete strength but is prohibitively expensive for most general field use. Another method of obtaining a sample that can be accurately tested for strength is to drill a core sample from the actual work at the desired time, using a diamond-core drill. While this method produces an accurate sample, it also is quite expensive and takes a long time to complete. Additionally, core drilling can be dangerous if the core is drilled in the wrong location, cutting reinforcing steel or post-tensioning cables. Core drilling is also a messy procedure due to the water that is used to cool the drilling bit. Typically, at the present time, core drilling is used only in certain limited circumstances, such as to verify low strengths that have been reported by other testing means.

It is therefore an object of the present invention to provide a method and apparatus for producing a test sample of concrete that has been cured in conditions identical to those in which the field piece has been cured. It is a further object of the invention to provide such a sample by a method that is quick and easy to use and also relatively inexpensive when compared to present methods.

SUMMARY OF THE INVENTION

In order to achieve the above-stated objects, the present invention utilizes a thin-walled mold placed directly into the concrete form. The mold is filled simultaneously with the form and is surrounded by the concrete of the actual member being poured so that it cures identically to the actual member. The mold contains an insert that is of an area the same as the interior cross-sectional area of the thin-walled mold and is spaced from the bottom of the mold to provide a space between the poured concrete and the bottom of the mold. A fluid inlet is formed in the mold to allow fluid to enter the space at the bottom of the mold. A fluid tube has an outlet end that is in fluid communication with the fluid inlet in the test mold and an inlet end that is adjacent or protrudes from the surface of the concrete in the form. When the concrete has cured to the point where an operation is to be done, such as tilting the slab, removing forms, et cetera, and there is a need to test the strength of the concrete, a fluid, such as compressed air, can be applied through the tube to pressurize the space at the bottom of the test mold, forcing the insert out from the slab under air pressure and, with it, the concrete sample which was poured in the mold. Once the sample is removed from the mold it can then be taken to a testing laboratory and tested by conventional methods.

In one embodiment, the insert has support members, such as legs, affixed thereto that are sufficiently strong to maintain the spacing of the insert from the bottom of the mold under the weight of the concrete being poured into the mold. The support members or legs should also be discontinuous to allow the flow of the pressurized fluid evenly throughout the bottom of the mold to provide an even pressurization of the space to force the test sample out of the mold.

In another embodiment, the insert is supported by a noncompressible fluid or viscous gel. A second nozzle and tube are provided in fluid communication with the space between the bottom of the mold and the insert. When it is desired to remove the test sample, a pressurized fluid, such as compressed air, is forced into the first nozzle and tube and the noncompressible fluid is forced out of the second nozzle. When all of the noncompressible fluid has been removed, the second nozzle is sealed and the compressed air pressurizes the space beneath the insert and forces the insert and sample out of the mold as described above for the first embodiment.

BRIEF DESCRIPTION OF THE DRAWINGS

The invention will be better understood by those of ordinary skill in the art, upon reading the ensuing specification, when taken in conjunction with the appended drawings, wherein.

DETAILED DESCRIPTION OF THE PREFERRED EMBODIMENT

Figure 1:
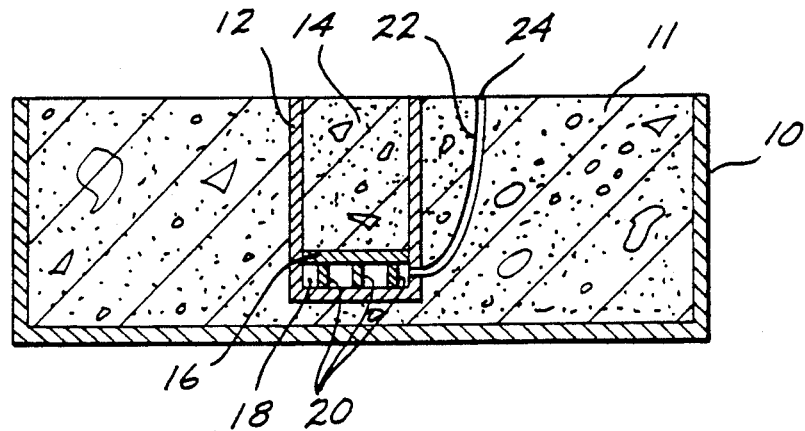
FIG. 1 is a side elevational view of a concrete slab within a form having one embodiment of a test mold made in accordance with the principles of the present invention inserted therein.

FIG. 1 shows a concrete form 10 that has been filled with concrete in the process of forming a slab 11. A cylindrical test mold 12 has been placed in the form, spaced from the bottom of the form, and filled with concrete, at the same time that the form 10 has been filled, to form a test sample 14. An upper edge of the test mold 12 is at the same level as the upper edge of the form 10 so that the top of the test cylinder 14 is at the same level as the top of the slab 11. An insert disk 16 has been placed in the test mold 12 spaced from the bottom wall of the mold 12 to provide a pocket 18 capable of being pressurized by a fluid. A plurality of legs 20 are integrally formed with the disk 16 and are used to support the disk in its spaced relation from the bottom wall of the test mold 12. The legs 20 are discontinuous with one another to provide a path for fluid to flow between and around the legs in order to completely fill the space 18. A fluid inlet is formed in a sidewall of the mold 12. A fluid tube 22 is connected at a first end to the fluid inlet of the test cylinder 12 and is in fluid communication with the space 18. A second end of the fluid tube 22 is adjacent the upper surface of the slab 11 so that it can be accessed at the top of the slab.

In actual operation, the slab 11 and the test sample 14 are poured simultaneously at the jobsite. The test sample 14 then is allowed to remain in place in the slab 11 as the concrete cures and is subjected to the identical conditions in the curing process as slab 11. When it is desired to remove the sample 14 for testing in a laboratory, a source of pressurized fluid (not shown), such as compressed air, is attached to a nozzle 24 at the second end of the fluid tube and the fluid is forced through the tube 22 into the space 18. The space 18 is pressurized by the fluid, causing a force to be applied against the insert disk 16. The insert disk 16 is forced upwardly as pictured in FIG. 1, which in turn forces the core sample 14 upwardly so that it can be removed from the test mold 12. Possibly, prior to pouring, some releasing agent typically used in concrete construction might be applied to the inner walls of the test mold 12 so that the core sample 14 could be more easily removed. Once the disk 16 has moved sufficiently upwardly to push the core sample 14 out of the mold, the core sample can be taken to a laboratory for testing. The space left in the concrete slab 11 by removal of the core sample 14 could be filled with a nonshrink grout and, since the size of the test sample would not be very great in comparison to the overall size of the slab, the strength of the slab would not be affected. Alternatively, the test mold 12 could be placed in the slab at a location where a hole was to be drilled later. In that situation, removal of the test sample 14 would leave behind a hole in a desired location so that the drilling would have to take place through only the remainder of the slab 11 below the test mold 12. In fact, the test mold could be made with breakaway spacer portions so that it could be used in slabs of different thickness. In this manner, two advantages would be accomplished; first a test core sample that was cured in situ would be provided and, also, hole drilling would be minimized for at least one location in the slab.

Figure 2:
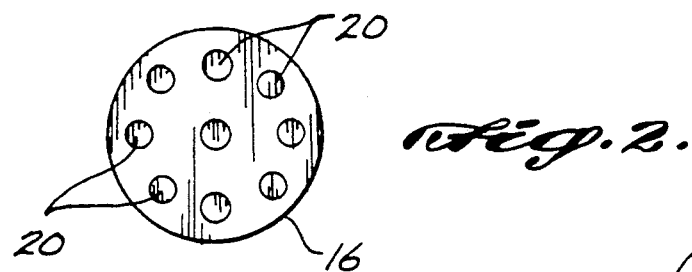
FIG. 2 is a bottom view of one embodiment of an insert for use with the test mold of FIG. 1.

FIG. 2 is a bottom view of insert 16 pictured in FIG. 1. The legs 20 are comprised of a plurality of rods spaced about the undersurface of the disk 16 to provide sufficient support to the disk so that it will not be collapsed by the weight of the concrete. The legs 20 also provide discontinuity that allows fluid to flow through the space 18 to provide even fluid pressure on the bottom of the disk 16.

Figure 3:
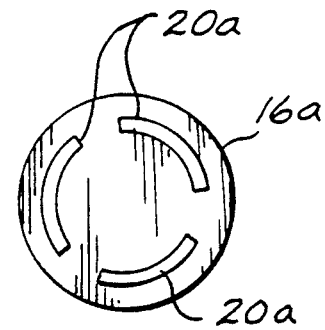
FIG. 3 is a bottom view of a second embodiment of an insert suitable for use with the test mold of FIG. 1.

FIG. 3 shows an alternative embodiment of an insert 16a in which the legs 20a are in the form of arcs of a circle positioned circumferentially around the insert to provide support but also to provide the discontinuity necessary to allow even fluid pressure to be applied to the undersurface of the disk.

Figure 4:
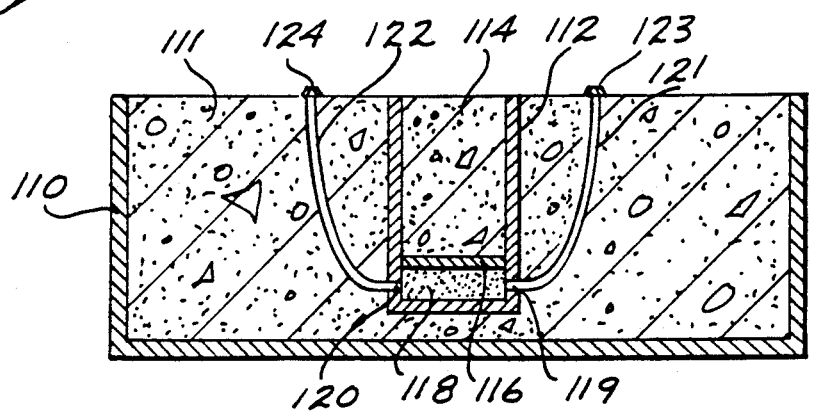
FIG. 4 is a side-elevational view of a concrete slab within a form having another embodiment of a test mold made in accordance with the principles of the present invention inserted therein.

FIG. 4 illustrates another embodiment of the test mold of the present invention. In FIG. 4, a concrete form 110 is filled with concrete in the process of forming a slab 111. A cylindrical test mold 112 is placed in the form so that the top of the mold 112 is flush with the top of the slab 111. The mold 112 is filled with concrete at the same time that the form 110 is poured to form a test sample 114. An insert disk 116 has been placed in the test mold 112 spaced from the bottom wall of the mold to provide a pocket 118. The pocket 118 is filled with a noncompressible fluid or gel that supports the disk 116 and the concrete above it. A first fluid inlet 119 is formed in the sidewall of the mold 112 and is in fluid communication with the pocket 118. A second fluid inlet 120 is formed in the sidewall of the mold 112 also in fluid communication with the pocket 118. A first fluid tube 121 is attached at a first end to the first fluid inlet 119 and a second fluid tube 122 is attached at a first end to the second fluid inlet 120. The second ends of the fluid tubes 121 and 122 extend to the surface of the slab 111. Preferably, valves 123 and 124, respectively, are connected to the second ends of the tubes 121 and 122.

When the concrete test sample has cured for the desired time, it is removed from the test mold. A source of pressurized fluid, such as compressed air, is attached to the second end of tube 121 and the valve 123 is opened to admit the air to the pocket 118. The valve 124 is opened and, as the air fills the pocket 118, the noncompressible fluid is forced from the pocket 118 through the tube 122. When all of the noncompressible fluid has been removed, as indicated by air being present in the tube 122, the valve 124 is closed. The compressed air continues to flow into the pocket 118 and pressurizes the pocket until the insert 116 and test sample 114 are forced out of the mold 112.

It will be understood that, although the tubes 121 and 122 are pictured on opposite sides of the mold 112, this is only for illustrative purposes and in actual practice the tubes could be closely adjacent one another. Also, as discussed above with regard to FIG. 1, the tubes 121 and 122 could exit the form 110 at the side or the bottom and do not have to be at the top of the slab.

Figure 5:
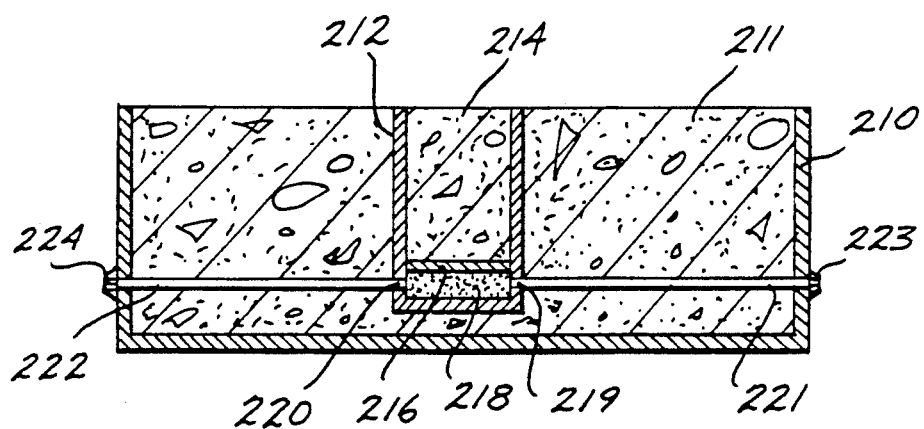
FIG. 5 is a side elevational view of a concrete slab within a form having an alternative embodiment of a test mold made in accordance with the principles of the present invention inserted therein.

FIG. 5 shows the alternative embodiment of the mold having the inlet and outlet tubes from the pressurization space exiting through the form, rather than to the top of the slab. Referring now to FIG. 5, a concrete form 210 is filled with concrete in the process of forming a slab 211. A cylindrical test mold 212 is placed in the form so that the top of the mold 212 is flush with the top of the slab 211. The mold 212 is filled with concrete at the same time that the form 210 is poured to form a test sample 214. An insert disk 216 has been placed in the test mold 212, spaced from the bottom wall of the mold, to provide a pocket 218. The pocket 218 is filled with a noncompressible fluid or gel that supports the disk 216 and the concrete above it. A fluid inlet 219 is formed in the sidewall of the mold 212 and is in fluid communication with the pocket 218. A fluid outlet 220 is formed in the sidewall of the mold 212, also in fluid communication with the pocket 218. A fluid tube 221 is attached at a first end to the fluid inlet 219 and a second fluid tube 222 is attached at a first end to the fluid outlet 220. The second ends of the fluid tubes 221 and 222 extend horizontally, as viewed in FIG. 5, to the sidewalls of the form 210. The fluid tubes 221 and 222 extend through openings in the sidewalls of the form 210 to the open air. Preferably, valves 223 and 224, respectively, are connected to the second ends of the tubes 221 and 222.

As in the embodiment shown in FIG. 4, when the concrete test sample has cured for the desired time, it is removed from the test mold. A source of pressurized fluid, such as compressed air, is attached to the second end of the tube 221 and the valve 223 is opened to admit the air to the pocket 218. The valve 224 is opened and, as the air fills the pocket 218, the noncompressible fluid is forced from the pocket 218 through the tube 222. When all of the noncompressible fluid has been removed, as indicated by air being present in the tube 222, the valve 224 is closed. The compressed air continues to flow into the pocket 218 and pressurizes the pocket until the insert 216 and the test sample 214 are forced out of the mold 212.

It should be understood that the pictured embodiments are exemplary only and that several changes can be made to the illustrated embodiments, while remaining within the scope of the invention. Although a cylindrical test mold 12 is shown in FIG. 1, the test mold could be of any closed shape with a variety of cross sections, such as a square, a rectangle, or even a hexagon. In such situations, the insert used to define the pressurization space at the bottom of the mold would be of geometric shape matched to the particular cross section of the test mold. Further, while the mold 12 is shown in a vertical orientation in FIG. 1, it would also be possible to have the mold inserted into the slab horizontally from either side, as long as an edge of the mold would be even with the surface of the slab for ease of removal. Also, the fluid tube 22 could be oriented in any direction so that the nozzle 24 protrudes from the side or even the bottom of the slab 11, with the only requirement being that the nozzle be accessible to a supply of compressed fluid when it is desired to remove the sample 14 from the test mold 12. In certain situations, such as in highway construction, it would be possible to place several of the test molds 12 into a section of the concrete highway and leave them in place for long periods of time, even years, for later removal simply by accessing the nozzles that would be marked on plans completed at the time of the pour. The test samples could be removed as desired for testing without the need for drilling or other expensive construction methods.

The actual test mold itself can be manufactured from many different materials, depending on the particular application. For most applications, such as floor slabs in buildings or tilt-up panels, the test mold can be made from a thin plastic much like the current laboratory test cylinders in use today. It may be necessary to place some exterior stiffener around the upper portion of the mold in order to ensure that the mold retains its shape during the placement of concrete. In situations that require a much larger mold, such as placement deep inside a concrete dam, it may be necessary to have relatively massive steel-walled molds in order to resist the forces caused by the weight of concrete or hydraulic pressure in underwater projects. Likewise, in certain projects, compressed air may not be a satisfactory fluid to force the sample from the test mold and it may be necessary to use other materials, such as hydraulic fluid, in order to achieve pressure sufficient to force the sample from the test mold.

Since so many changes can be made to the illustrated embodiments without exceeding the scope of the invention, it is necessary to define the invention solely by reference to the appended claims.

The embodiments of the invention in which an exclusive property or privilege is claimed are defined as follows:

1. A mold for producing test samples of concrete comprising:
   a closed self-supporting sidewall;
   a bottom wall attached to said sidewall;
   a movable insert placed within said sidewall above said bottom wall to define a pressurization chamber between said insert and said bottom wall;
   a fluid inlet in said mold in fluid communication with said pressurization chamber; and
   a fluid inlet tube connected at a first end thereof to said fluid inlet and connectable at a second end to a source of pressurization fluid.

2. The mold of claim 1, further including spacer means between said insert and said bottom wall to maintain a spacing of said insert from said bottom wall.

3. The mold of claim 2, wherein said spacer means comprises legs affixed to said insert.

4. The mold of claim 3, wherein said legs are separated from one another to allow fluid to flow between them.

5. The mold of claim 2, wherein said spacer means is a noncompressible fluid.

6. The mold of claim 5, wherein said spacer means is a viscous gel.

7. The mold of claim 5, further including:
   a fluid outlet port formed in said mold in fluid communication with said pressurization chamber; and
   a fluid outlet tube connected at a first end to said fluid outlet port, said fluid outlet tube being of at least sufficient length to reach to the top of said mold sidewall.

8. The mold of claim 7, wherein said fluid outlet tube has a valve connected to its second end.

9. The mold of claim 5, further including:
   a form for concrete surrounding said mold;
   a fluid outlet port formed in said mold in fluid communication with said pressurization chamber; and
   a fluid outlet tube connected at a first end to said fluid outlet port, said fluid outlet tube being of a length at least sufficient to reach an exterior surface of said form.

10. The mold of claim 9, wherein said fluid outlet tube has a valve connected to its second end.

11. The mold of claim 5, further including outlet means affixed to said mold and in fluid communication with said pressurization chamber to permit the removal of said noncompressible fluid from said pressurization chamber.

12. The mold of claim 1, wherein said fluid inlet tube is of a length at least sufficient to reach the top of the mold sidewall.

13. The mold of claim 1, wherein a second end of said inlet tube has a fluid coupling attached thereto.

14. The mold of claim 1, wherein said insert is congruent to the cross section of said mold.

15. The mold of claim 1, further including a form for concrete surrounding said mold, the fluid inlet tube being of a length at least sufficient to reach an exterior surface of said form.

* * * * *